United States Patent [19]

Båvik et al.

[11] Patent Number: 5,573,939
[45] Date of Patent: Nov. 12, 1996

[54] DNA ENCODING MAMMALIAN RETINOL BINDING PROTEIN RECEPTOR, AND CORRESPONDING VECTORS AND TRANSFORMED CELLS

[75] Inventors: Claes O. Båvik; Ulf Eriksson, both of Stockholm, Sweden; Per A. Peterson, La Jolla, Calif.

[73] Assignee: Ludwig Institute For Cancer Research, New York, N.Y.

[21] Appl. No.: 200,807

[22] Filed: Feb. 22, 1994

Related U.S. Application Data

[63] Continuation of Ser. No. 883,539, May 15, 1992, abandoned.

[51] Int. Cl.$^6$ ............................ C12N 15/12; C12N 15/63; C12N 5/10
[52] U.S. Cl. ........................ 435/240.2; 435/320.1; 435/69.1; 435/254.11; 536/23.5
[58] Field of Search ..................... 536/23.5; 435/320.1, 435/240.2, 69.1, 252.3, 254.11

[56] References Cited

U.S. PATENT DOCUMENTS 4,675,285  6/1987  Clark et al. ................................. 435/6

OTHER PUBLICATIONS

Akustrom et al., TIBS 15:240–243 (Jun. 1990).
Flower et al., Biochem. & Biophys. Res. Comm. 180(1):69–74 (Oct. 15, 1991).
Nutr. Rev. 49:218–221 (1991).
Young, R. A., et al. (1983) Proc. Natl. Acad. Sci. USA 80:1194–1198.
Båvik, C. O., et al. (1991) J. Biol. Chem. 266:14978–14985.
Sivaprasadarao, A., et al. (1988) Biochem. J. 255:561–569
Pfeffer, B. A., et al. (1986) Invest. Ophthalmol. Vis. Sci. 27:1031–1040.
Mui, A. L., et al. (1992) J. Biol. Chem. 267:16523–16530 (Medcine abstract).
Watson, J., et al. (1992) *Recombinant DNA*, New York: Scientific American, pp. 222–224.

*Primary Examiner*—David L. Fitzgerald
*Attorney, Agent, or Firm*—Felfe & Lynch

[57] ABSTRACT

Isolated receptors for lipocalins and retinol binding proteins are disclosed, as are nucleic acid sequences coding for these molecules, and antibodies which bind to these receptors. Various uses of these materials are described as well.

10 Claims, 9 Drawing Sheets

DNA ENCODING MAMMALIAN RETINOL BINDING PROTEIN RECEPTOR, AND CORRESPONDING VECTORS AND TRANSFORMED CELLS

This application is a continuation of application Ser. No. 07/883,539, filed May 15, 1992, now abandoned.

FIELD OF THE INVENTION

This invention relates to receptors for the class of molecules known as lipocalins. In particular, it relates to receptors which bind to retinol binding protein. Most particularly, a protein referred to as RBPr, an abbreviation for "retinol binding protein receptor" is described, which is isolated from the retina. The invention involves isolated proteins, monoclonal and polyclonal antibodies which specifically bind to the proteins, as well as isolated nucleic acid sequences coding for or complementary to coding sequences therefor. It also relates to various applications of these materials.

BACKGROUND AND PRIOR ART

During recent years it has become evident that retinoids (vitamin A-derivatives) have a variety of biological functions. Most of the interest concerning retinoids has been to focus on the role of retinoic acid (RA) during embryogenesis and in particular on the role of RA in pattern formation of the vertebrate limb (Tabin, *Cell* 66:199–217 (1991)). However, it is well established that retinoids play important roles in other normal physiological functions; for example retinoids have been shown to be important for normal differentiation and growth of several epithelia including skin (Fuchs, *J. Cell Biol.* 111:2807–2814 (1990)). The recent identification of nuclear RA-receptors (Benbrook et al., *Nature* 333: 669–672 (1988); Brand et al., *Nature* 332: 850–853 (1988); Giguere et al., *Nature* 330:624–629 (1987); Krust et al., *PNAS* 86: 5310–5314 (1989); Mangelsdorf et al., *Nature* 345: 224–229 (1990); Petkovich et al., *Nature* 330:444–450 (1987); Zelent et al., *Nature* 339: 714–717 (1989)) have demonstrated that the nonvisual function of retinoids, i.e., RA, is to control transcription of specific genes and a number of such genes have been identified (de The et al., *Nature* 343:177–180 (1990); Duester et al., *Mol. & Cell Biol.* 11: 1638–1646 (1991); La Rosa et al., *PNAS* 85:329–333 (1988); La Rosa et al., *Mol. & Cell Biol.* 8: 3906–3917 (1988); Nicholson et al., *EMBO J* 9:4433–4454 (190); Vasios et al., *PNAS* 86:9099–9103 (1989)).

The mechanisms involved in controlling the level of RA available to the nuclear RA-receptors are less well known but it is known that under normal physiological conditions most cells obtain retinoids as retinol. The extracellular transport of retinol is carried out by the plasma retinol-binding protein (RBP) (Goodman, in Sporn et al., Eds. *The Retinols:* 41–88 (Academic Press, 1984)). This 21 KDa protein is well characterized and both the primary and tertiary structures are known (Newcomer et al., *EMBO J* 3: 1451–1454 (1984); Rask et al., *FEBS Letters* 104: 55–58 (1980)). RBP is structurally related to a number of extracellular proteins involved in the transport of small hydrophobic compounds, called the lipocalins (Pervaiz et al., *FASEB J* 1:209–214 (1987)). Well known members of the lipocalin group of protein include β-lactoglobulin (Godovach-Zimmerman et al., Hoppe-Seyler Biological Chemistry 366:431–434 (1985)) apolipoprotein D (Drayna et al., *J. Biol. Chem.* 261: 16535–16539 (1986)), olfactory binding protein (Lee et al., *Science* 235:1053–1056 (1987)) and protein HC (Lopez et al., Biochem. & Biophys. Res. Comm. 103:919–925 (1981)).

The details of how retinol is transferred from RBP to cells are not known. However, the specific transfer to a restricted number of cells and cell types suggest a receptor mediated mechanism. The presence of RBP-receptors has been recognized on several cell types (Båvik et al., *J. Biol. Chem.* 266:14978–14985 (1991); Eriksson et al., *Canc. Res.* 46:717–722 (1986); Heller, J. Biol. Chem. 250:3613–3619 (1975); McGuire et al., Endrocrin 108: 180–188 (1981); Rask et al., *J. Biol. Chem.* 251:6360–6366 (1976); Sivaprasadarao et al., *J. Biochem. J.* 255: 561–569 (1988)). Recently a membrane binding assay was developed by which some of the characteristics of a RBP membrane receptor expressed in bovine retinol pigment epithelium (RPE) were revealed (Båvik et al., supra, Eriksson et al., supra). Some partial purification of this receptor is disclosed in U.S. Ser. No. 740,006 filed Aug. 2, 1991, now abandoned.

Monoclonal and polyclonal antibodies to proteins which are receptors for retinol binding protein have now been found useful in securing pure RBPr from RPE cells. This molecule is characterized by a molecular weight of about 63 KDa, as determined by SDS-PAGE. In addition, complementary DNA ("cDNA") has been isolated which codes for these lipocalin receptors, especially the RBPr. This DNA has been incorporated into plasmids, and has been successfully translated in vitro. These, as well as other aspects of the invention are elaborated upon in the disclosure which follows.

BRIEF DESCRIPTION OF THE FIGURES

FIG. 1A shows a crosslinked complex of 86 kDa, bound to the monoclonal antibody ("mAb") A52. Free retinol binding protein ("RBP") eluted out, in unbound fractions. Note lanes c and d. FIG. 1B shows Coomassii staining of both eluted and unbound fractions, and shows that a 63 kDa protein was eluted off the column. In FIG. 1C, the eluted material was immunoblotted with mAb A52, and the figure shows a reaction between mAb A52 and the 63 kDa protein.

FIG. 2A shows that complexes of RBP.RBPr remain attached to membranes following extraction, while FIG. 2B shows washing off of 63 kDa protein.

BRIEF DESCRIPTION OF THE SEQUENCES

SEQUENCE ID NO: 1 shows cDNA together with amino acid sequence for RBPr molecule.

SEQUENCE ID NOS: 2–5 present 5' extensions for the cDNA molecule of SEQ ID NO: 1.

DETAILED DESCRIPTION OF PREFERRED EMBODIMENTS

EXAMPLE 1

In order to carry out the type of analysis desired, monoclonal antibodies to a retinol binding protein receptor ("RBPr" hereafter) were generated. To do so, BALB/c mice received footpad injections in their hindlimbs, using bovine retinal pigment epithelium ("RPE" hereafter) microsomes, emulsified in Freunds complete adjuvant as immunogen. Each mouse received 10 ug of total microsomal protein in a 50 ul volume. Ten days later, popliteal lymph nodes were collected, separated into individual cells, and fused with SP/2 myeloma cells. The procedure followed was standard, as per Holmdahl et al., *J. Immunol. Meth.* 83: 379–386 (1985), the disclosure of which is incorporated by reference.

Ten days after the fusion, hybridomas were screened using an enzyme immunoassay, as described herein. One hundred ul of RPE-microsomes were suspended in 100 mM sodium bicarbonate buffer, pH 9.5, to a concentration of 25 ug of total microsomal protein per ml and coated onto microtiter plates overnight at 4° C. The plates were then washed using phosphate buffered saline (PBS), and then 100 ul of supernatant from the hybridoma cultures were added. Incubation for two hours at room temperature followed, and this was followed by several washings in PBS to displace non-specific binding. In order to visualize bound mAbs, alkaline phosphatase (ALP) labelled anti-Ig was added. Clones displaying reactivities at least five times greater than background were selected, expanded in 12 well plates, and further characterized.

The selected clones were further characterized using immunoblotting studies. To do this, RPE-microsomes were suspended in SDS loading buffer, reduced, alkylated, and presented on SDS-PAGE, using 10% linear slab gels. Separated proteins were blotted onto nitrocellulose, and non specific protein binding was blocked by overnight incubation in PBS containing 3% nonfat dry milk and 2% bovine serum albumin. Filters were cut in 2–3 mm wide strips, and were separately incubated in culture supernatants for two hours at room temperature. Extensive washing in PBS containing 0.1% Tween 20 followed, and then the filter strips were incubated for one hour in the blocking solution described supra, with goat antimouse IgG antibodies labelled with alkaline phosphatase. Following washing, bound Ig was visualized.

Some of the hybridomas producing mAbs which bound to protein in the Mr 60–65 KDa range were expanded and subcloned via limited dilution.

EXAMPLE 2

The monoclonals subjected to limited dilution subcloning as described supra were tested to analyze their ability to immunoprecipitate RBP receptor. To do so, aliquots of crosslinked RBP-RBPr complexes were solubilized in 1% "CHAPS" (3-[(3-cholamidopropyl)-dimethyl ammonio]-1-propane sulfonate) in PBS, and subjected to indirect immunoprecipitation using 1 ml of culture supernatant per incubation. (The concentrations of CHAPS were maintained at 1% throughout by adding from a 10% stock solution). Following 4 hours of incubation on ice, Ig was collected via addition of 100 ul of 10% suspension of PANSORBIN® (immunoglobulin binding *S. auerus* cells). Immunoprecipitates were washed three times in 1% CHAPS in PBS, and were analyzed by SDS-PAGE, using 5–10% gradient gel slabs, following Bavik et al., *J. Biol. Chem.* 266:14978–14985 (1991). Gels were exposed for one week at –70° C., using intensifying screens.

Of the positive clones identified via the approach set out herein, hybridoma A52 was selected for further analysis. Hybridoma cell line A52 has been deposited in accordance with the Budapest Treaty. A deposit was made to the Collection Nationale de Cultures de Microorganismes, Institut Pasteur, on May 14, 1992, and is identified by Accession number 1–1208. To have mAbs available for further study, the hybridoma was expanded in culture, injected into Pristane primed Balb/c mice, and ascites was collected. IgG was isolated using Protein A SEPHAROSE® (high molecular weight material for gel filtration of macromolecules) and well known techniques not repeated here.

EXAMPLE 3

Monoclonal antibody A52, described supra, was used to characterize one retinol binding protein receptor (RBPr) via immunoaffinity chromatography. To do this, either mAb A52 or preimmune rabbit IgG was coupled to CNBr activated Sepharose® 4B, using standard methodologies. The columns were contacted with RPE membrane fractions containing crosslinked, radiolabelled RBP which had been solubilized in 200–300 ul of 1% CHAPS in PBS for 30 minutes. These solutions were passed over the A52 or preimmune Ig column, and rinsing with 10 column volumes of 1% CHAPS in PBS followed. Any bound proteins were eluted by washing with 50 mM triethanolamine buffer, at pH 11.5, containing 1% CHAPS. The pH of eluate was adjusted to 8 by adding 1M Tris.HCl buffer, at pH 8. Eluted proteins were dialyzed against 1% CHAPS in PBS overnight, concentrated using Centricon® 30 (liquid filtering and solute concentrating unit) cells, and directly dissolved in SDS-PAGE loading buffer or stored at –70° C. until further used.

The materials were subjected to SDS-PAGE or autoradiography, using methods discussed above. Unlabelled proteins were stained with 0.1% Coomassie Brilliant Blue (R-250) dissolved in 5% acetic acid and 10% methanol in water. This solution, without Coomassie Blue, was used as destaining solution.

Figure 1A:
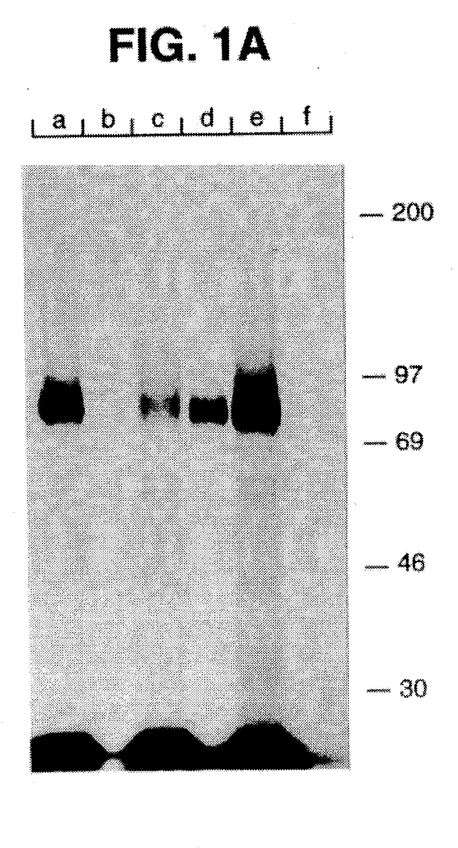
FIGS. 1A, 1B and 1C show SDS-PAGE analysis of protein bound to A52 immunoaffinity columns.
Figure 1B:
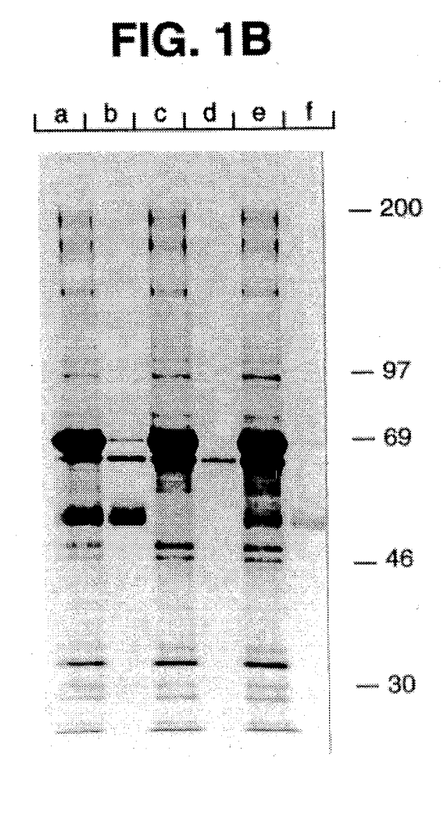

The results of these experiments are shown in FIGS. 1A and 1B. In FIG. 1A, it is shown that a crosslinked, 86 KDa complex bound to the immunocolumn containing A52 mAb, and free RBP eluted out in the unbound fraction Lanes "c" and "d" of FIG. 1A show this. Lanes "e" and "f" show that preimmune IgG did not retain this complex In FIG. 1B, lanes "d" and "f" Coomassie staining of eluted and unbound fractions, show that a bound protein of 63 KDa was eluted off the column, as compared to the preimmune IgG column.

EXAMPLE 4

Figure 1C:
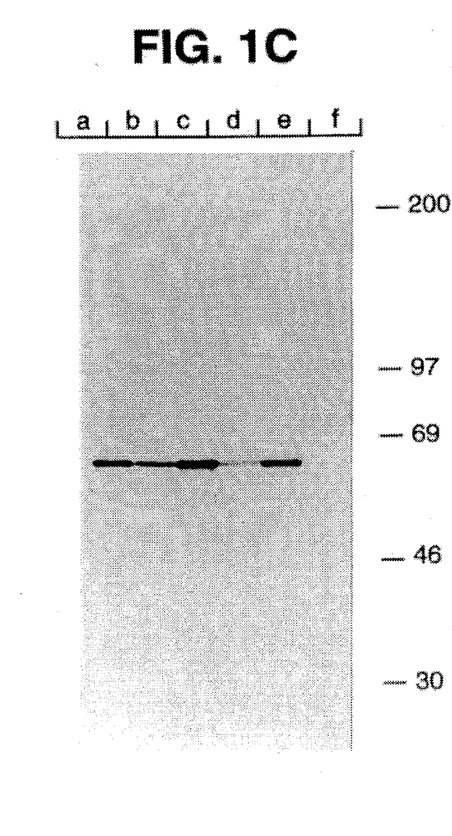

Further studies were carried out using the material eluted from the columns, as per Example 3. Specifically, immunoblotting was performed, following the immunoblot protocol given in Example 2, using 10 ug/ml of purified mAb A52. Results of these experiments are shown in FIG. 1C. Lane d of this figure shows that the A52 mAb recognized a 63 KDa protein in the eluate. Strong immunoreactivity was also obtained in unbound fractions from the A52 column and the preimmune IgG column (lanes c and e of the figure).

Further immunoblotting was carried out using rabbit polyclonal antibodies. These were prepared by immunization with highly purified RBPr (20 ug per rabbit), emulsified in Freunds Complete Adjuvant. The antigen was administered via intranodal injection, and the animals were administered subcutaneous booster injections every second week, using the same amount of antigen in Freunds incomplete adjuvant. Blood was collected and IgG was isolated via Protein A Sepharose. The antibodies were coupled to CNBr activated Sepharose 4, in the same manner as the mAbs of prior examples were coupled, and immunoblotting was carried out in the same manner as with the mAbs.

The results of immunoblotting with polyclonal antisera are shown in FIG. 1C, lanes "a" and "b". As with the mAbs, a 63 KDa protein was recognized as eluted material. This conclusion is borne out in FIG. 1A and 1B, lanes "a" and "b" of both figure, which showed that cross linked complex did not bind, whereas the 63 KDa protein eluted extensively. These data show that RBP, when bound to RPE membrane, is cross linked to a 63 KDa membrane protein.

The presence of cross-linked complex on the A52 column, with major portions of 63 KDa protein in eluted fractions, suggests that when solubilized in a deoxycholate containing buffer, the protein may occur in different conformations.

EXAMPLE 5

Experiments were carried out to extract RBPr using an alkaline solvent. Samples (50 ug total protein) of RPE membranes containing crosslinked, radiolabelled RBP were suspended in 1 ml of 100 mM sodium carbonate buffer (pH 11.5). This mixture was incubated on ice for 30 minutes, after which membranes were collected by centrifugation at 100,000 xg for 30 minutes and suspended in 100 mM Tris at pH 8.0. Supernatant was adjusted to pH 8.0 with 1 M Tris pH 8.0 and concentrated by ultra filtration using Centricon 30.

Figure 2A:
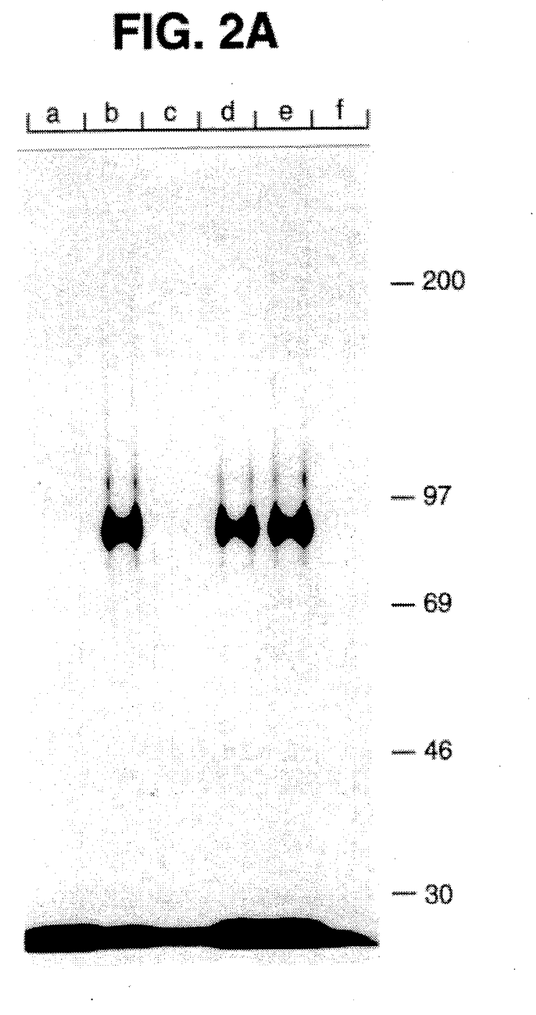
FIGS. 2A and 2B show results obtained following purification of retinol binding protein receptor ("RBPr") in alkaline solvent. These experiments involved suspending samples in an alkaline buffer followed by ultrafiltration.

This purification protocol quantitatively removes peripheral membrane proteins from membrane, while transmembrane proteins normally remain attached. FIG. 2A shows that the cross linked RBP.RBPr complex remains firmly attached to membranes following this extraction (lanes a and b; control was extraction with PBS; lanes c and d).

Figure 2B:
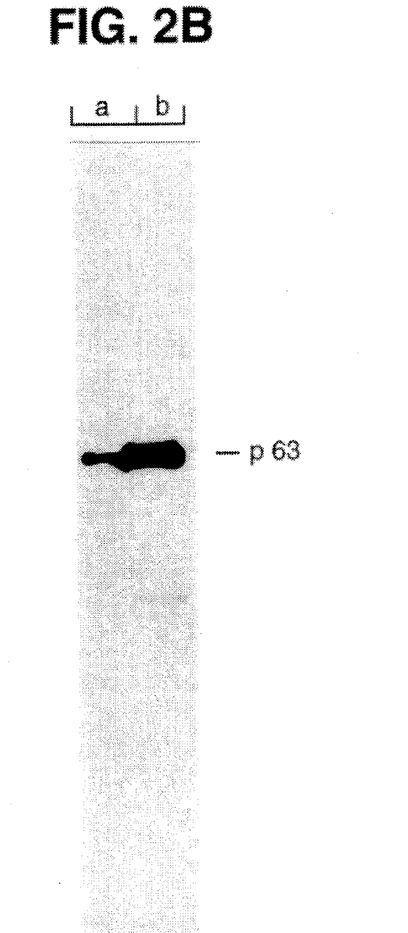

Further analysis showed, surprisingly, that a major portion of the 63 KDa protein was washed off the membrane, while a minor portion remained attached (FIG. 2B, lanes a and b).

Repeated extractions were carried out by resuspending membrane pellets from the centrifugation step in 1 ml 100 mM sodium carbonate buffer pH 11.5, and treated as described supra; however, even repeated extraction failed to remove all of the 63 KDa protein. This suggests that RBPr may occur in two forms; one of these, the major form, is loosely attached to RPE membranes, and another form is alkaline resistant. These results, taken with those discussed supra, suggest that the alkaline resistant form of RBPr has the ability to bind RBP, while alkaline sensitive receptor does not.

EXAMPLE 6

There was a possibility that the 63 KDa protein was not a genuine membrane associated protein. To investigate this possibility, identical amounts of protein from isolated membrane fractions and from RPE-cytosol fractions were subjected to SDS-PAGE. Coomassie staining showed a major 63 KDa band in membrane fractions, whereas cytosol showed no such material. These results were confirmed by immunoblotting.

EXAMPLE 7

The properties of the RBPr described supra are not those generally associated with regular transmembrane proteins. In view of this, investigation were carried out to determine whether crosslinked RBP-RBP receptor complex and RBPr were attached to membranes via fatty acid acylation. This was accomplished by hydrolysis of the complex and RBPr in the presence of hydroxylamine at pHs of 7.0 and 10.0. Thiolesters are cleaved at the neutral pH, and regular esters under the alkaline conditions. It was determined thereby that the 86 KDa crosslinked complex and RBPr were not detached from membranes by this treatment, suggesting that fatty acid acylation does not bind the complex or RBPr to membranes.

EXAMPLE 8

Figure 3A:
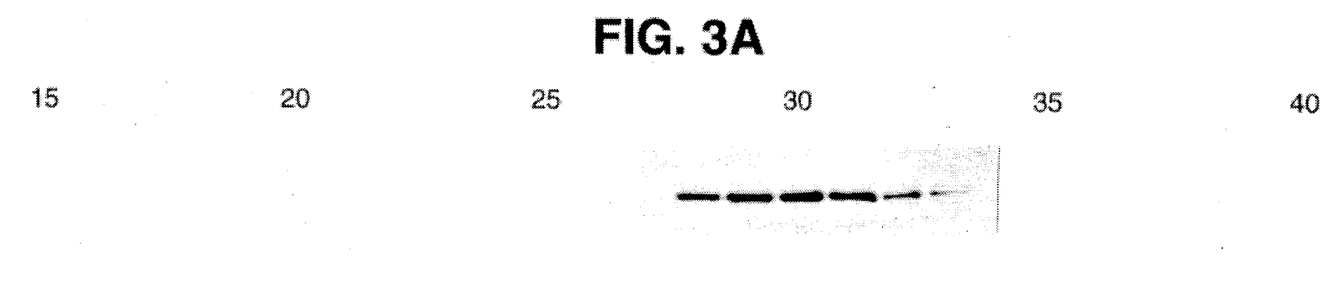
FIGS. 3A and 3B show results obtained following dissolution, ultracentrifugation and elution of membrane fractions, where the membrane fractions are from RPEs. Immunoblotting of deoxycholate solubilized protein is depicted.
Figure 3B:
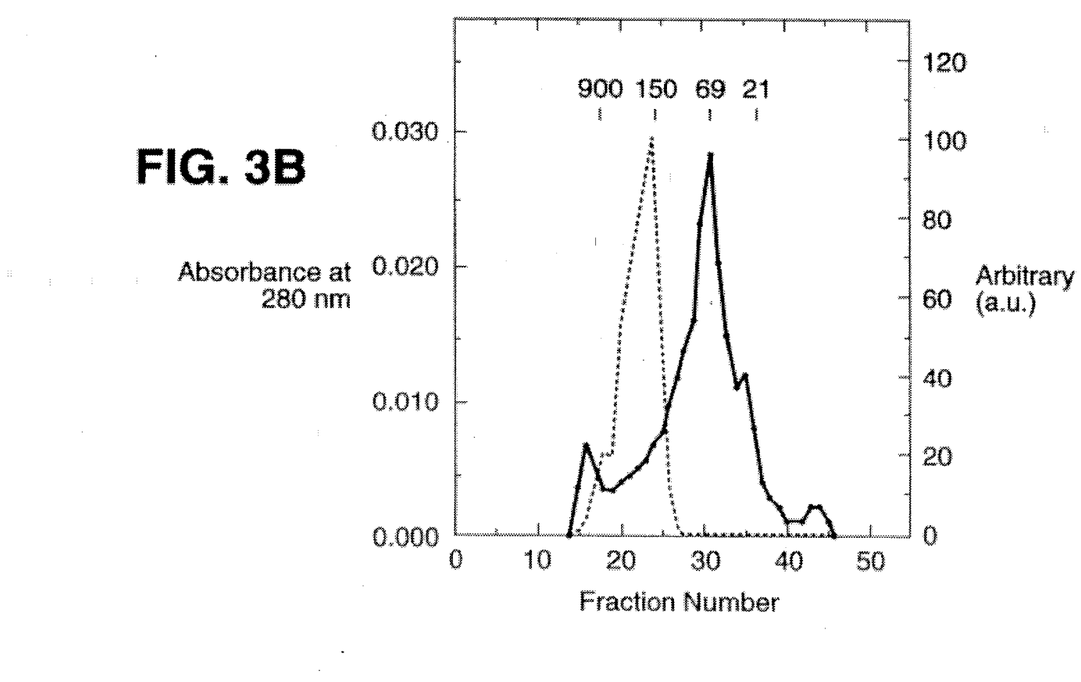

In order to characterize the size of the RBP.RBP receptor complexes and RPE, membrane fractions containing crosslinked radiolabelled RBP (20–40 ug of total membrane protein) were dissolved in 500 ul of buffer (10 mM deoxycholate, 20 mM Tris, pH 8.3, and 30 mM NaCl). Ultracentrifugation at 100,000 xg to remove debris followed and then samples were loaded onto a Superose 6 column (1×30 cm), connected to an FPLC system. Elution was carried out as described by Båvik et al. supra. Ten percent of each fraction was subjected to SDS-PAGE separation, and to immunoblotting using A52 mAb. Both procedures were as described supra. FIGS. 3A and 3B depict these results.

Elution profiles for IgM (900 KDa); IgG (150 KDa); and RBP (21 KDa), serve as "markers". Most of the RBPr eluted around fractions 29–31, the expected position for the monomeric receptor. Fractions corresponding to higher molecular weights, i.e., fractions 15–28, also showed RBPr. Cross linked 86 KDa fractions were found in fractions 15–27, a marked peak being found in fractions 23–25. The latter peak corresponds to globular protein of a molecular weight of about 150 KDa. These data again suggest at least two different forms of the molecule.

EXAMPLE 9

Figure 4:
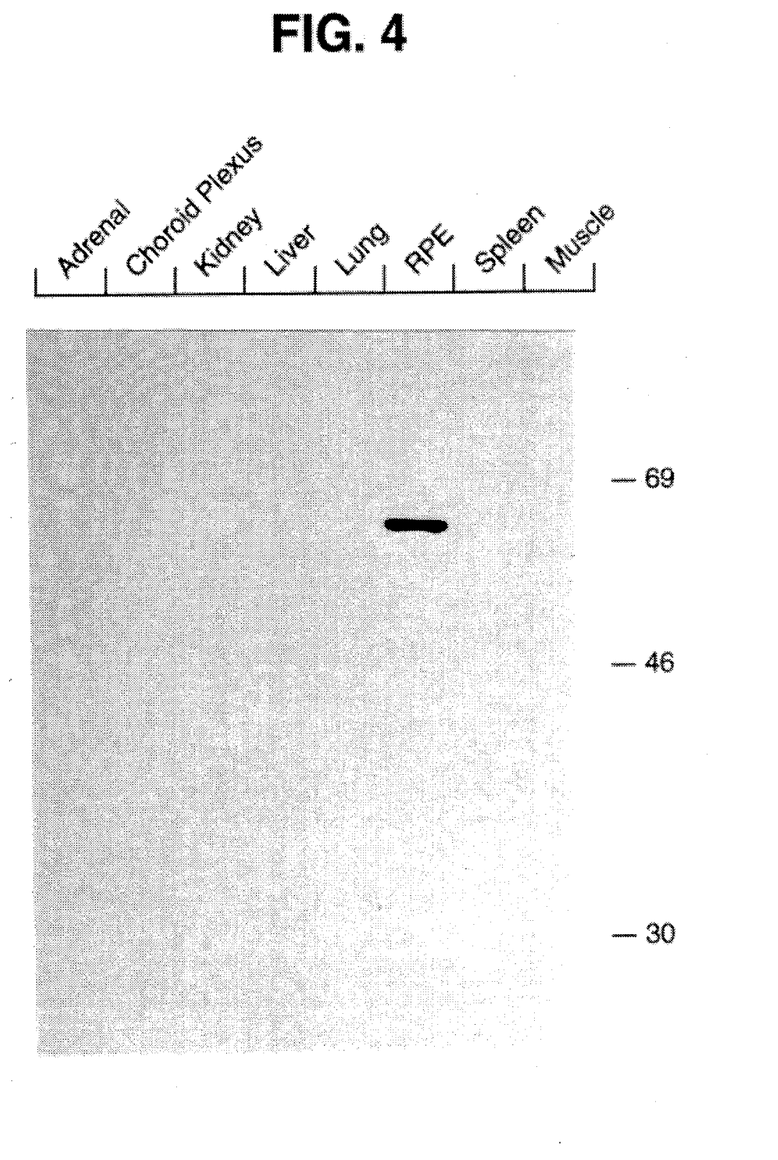
FIG. 4 shows results obtained when various tissues were tested for RBPr. The listed tissues were treated to secure membrane fractions, and were immunoblotted in the same way the samples were tested which are depicted in FIGS. 1A and 1B.
Figure 5A:
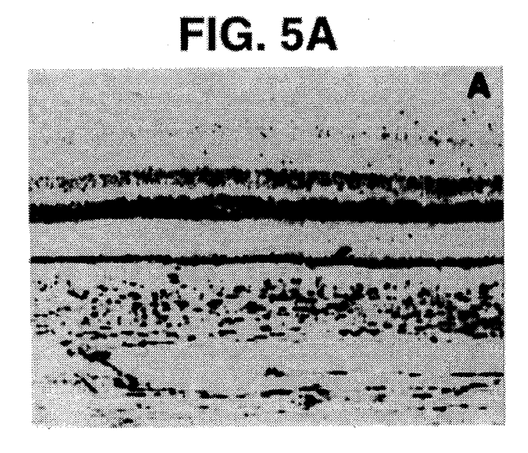
FIGS. 5A–5D depict the results of experiments undertaken to determine localization of the RBPr. Histochemical analysis was carried out, using an "ABC" system. The results are shown.
Figure 5B:
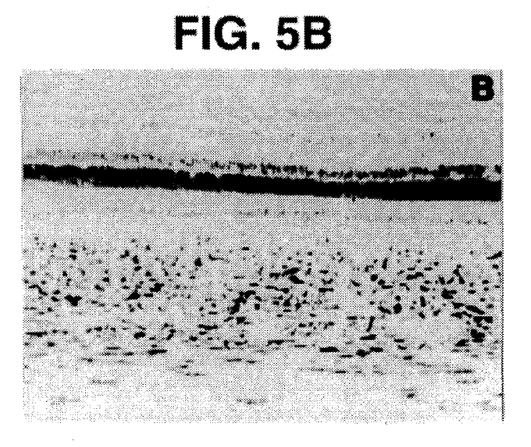
Figure 5C:
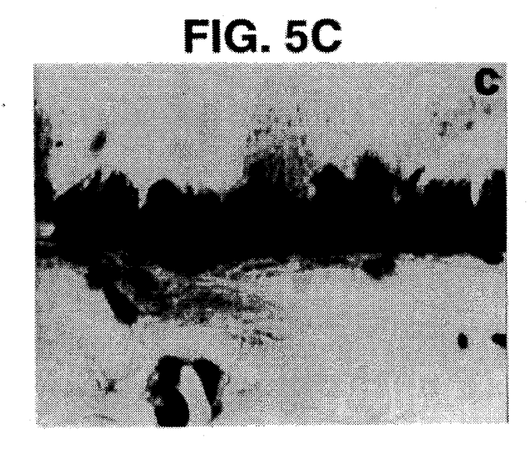
Figure 5D:
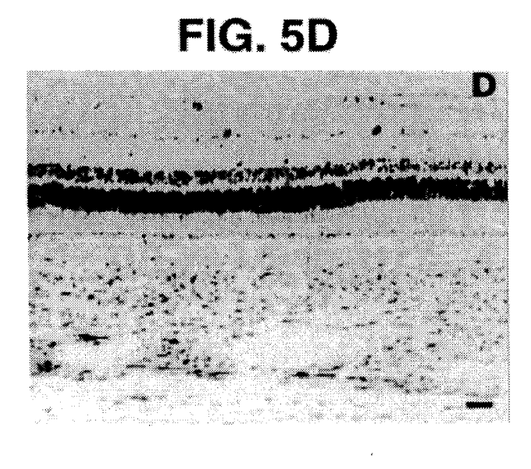

Tissue distribution of RBPr was investigated via immunoblotting, using membrane fractions derived from bovine adrenal gland, choroid plexus, kidney, liver, lung, RPE, spleen, and muscle. To carry out the analysis, 200 ug membrane fractions were subjected to SDS-PAGE, and blotted onto nitrocellulose filters. These were incubated with mAb A52 and anti-Ig antibodies labelled with alkaline phosphatase, as described supra. FIG. 4 presents these data, and shows that the complex was only identified in the RPE fraction.

EXAMPLE 10

Localization of the RBPr was carried out using immunohistochemical staining and the well known "ABC" or "avidin-biotin cascade" system. Freshly isolated bovine eyes were first injected at multiple sites with 4% formaldehyde in PBS. Retinas were immediately dissected into small pieces, and fixed overnight in this solution. The materials were embedded in paraffin, sectioned (7 um), and dewaxed. Following this, the ABC technique was carried out with staining in accordance with Busch et al., Meth. Enzymol. 189:315–323 (1990). Monoclonal antibody A52 was again used, at a concentration of 2 ug/ml, in an overnight incubation.

FIGS. 5A–5D show these results. The RBPr was only identified in bovine retina derived RPE cells. High magnification showed distribution through the cell bodies, presumably in endoplasmic recticulum. There is stronger staining in basolateral portions of the cells as well.

EXAMPLE 11

Figure 6A:
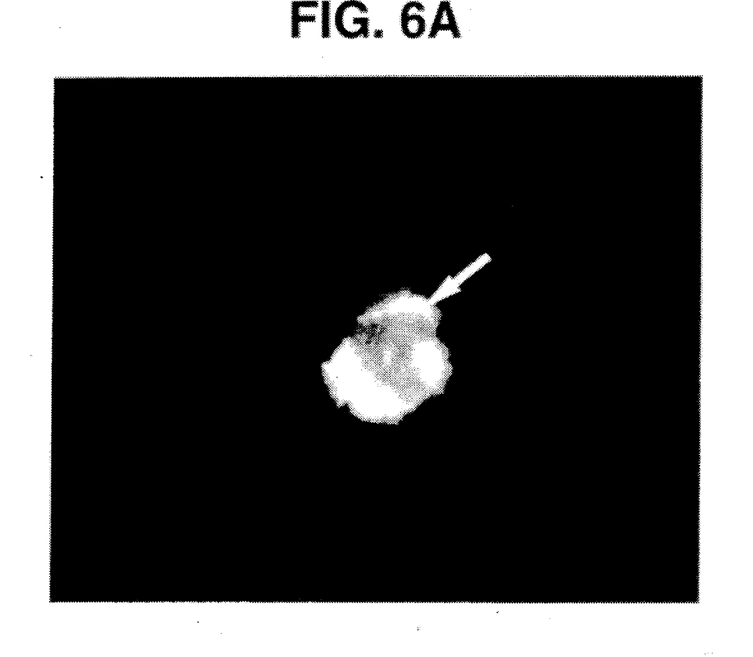
FIGS. 6A and 6B depict results obtained from experiments designed to localize the RBPr. Isolated RPE cells were fixed on cover slips, and RBPr localized via the use of mAb A52 and labelled anti-IgG.
Figure 6B:
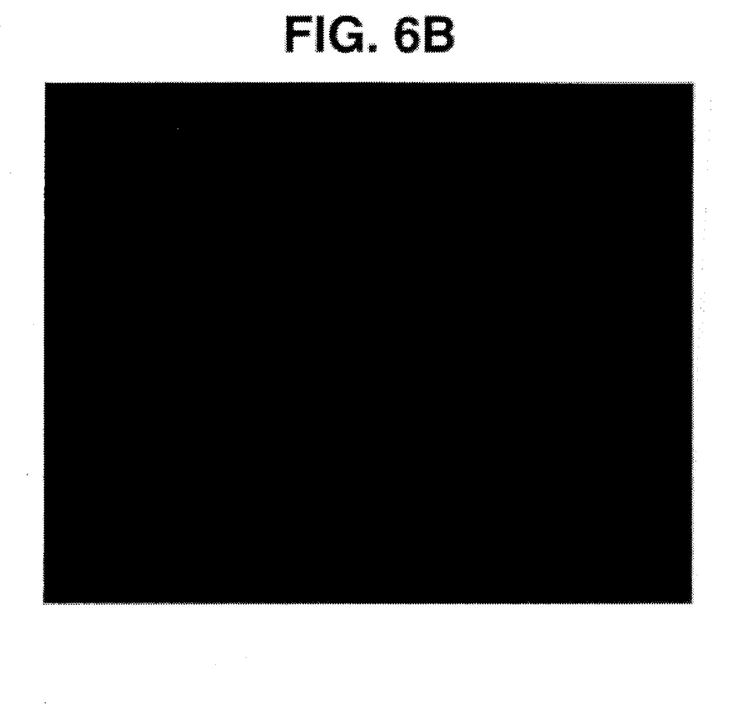

The work in Example 10 did not show a clear, cell surface localization for the receptor. As such, isolated RPE cells were grown on cover slips. These were fixed, but not permeabilized, via the use of 3% paraformaldehyde. Expression of the receptor was visualized using mAb A52 and anti-Ig labelled with tetramethylrhodamine isothiocyanate (TRITC). Control stainings used an unrelated mAb. At a magnification of 100x, as shown in FIGS. 6A and 6B, strong signals were obtained with A52, but not the control. This leads to the conclusion that RBPr is also exposed on RPE cell surfaces.

In subsequent experiments, cells permeabilized with 0.1% Triton-X-100 show a major fractions of the receptor localized in association with intracellular membranes.

EXAMPLE 12

Pure RBPr was recovered by binding it to an A52 immunoaffinity columns as in Example 3, supra. RPE-microsomes were solubilized in 1% CHAPS for 30 minutes on ice and debris was removed by centrifugation at 100,000xg for one hour at 4° C. The solubilized proteins were passed over the A52 column and the column was washed with five column volumes of 1% CHAPS in PBS, followed by desorption via washing with 50 mM triethanolamine buffer, pH 11.0, containing 1% CHAPS. Eluate pH was adjusted to 8 by addition of 1 M Tris-HCl buffer, pH 8. Eluted proteins were dialyzed against 1% CHAPS in PBS overnight, and concentrated in a Centricon 30 cell.

Fifty ug of highly purified RBPr was secured in this way, and was dissolved and denatured by boiling for two minutes in 10 ul of 2% SDS in 100 mM ammonium bicarbonate buffer, pH 7.5. SDS concentration was adjusted to 0.02% by adding buffer. After this, endoprotease Glu-C was added to yield an RBPr/protease molar ratio of 50:1. Digestion proceeded for two hours at 37° C., after which aliquots of digest were subjected to SDS-PAGE, followed by transfer to PVDF filters. The transferred peptides were visualized by staining with 1.25% Coomassie Brilliant Blue in 10% acetic acid and 50% methanol. Any peptides migrating as distinct bands were cut out of the filters, and amino acid sequences determined, following Hellman et al., Radola et al., in Electrophoresis Forum 89: 89–93 (1989). The sequence is presented in SEQ ID NO: 1, which follows these examples.

EXAMPLE 13

A cDNA sequence coding for RBPr was secured. To do this, a bovine RPE-cell specific cDNA library was constructed in lambda ZAP II vector using mRNA from RPE cells. This library was then used to express hybrid protein is in E. coli "Sure" bacteria, following induction with IPTG. In a first screen, 300,000 plaques were screened, using $^{125}I$ labeled, affinity purified IgG to RBPr, following Young et al., PNAS USA 86: 9099–9103 (1983). Radiolabelling was accomplished using chloramine T and $Na^{125}I$, following Hunter et al., Nature 194:495–496 (1962). Two rounds of rescreening followed, and clone R2A was found to give the most intense signal. The cDNA from this clone was excised, in vivo, using helper phage R408, and plasmid pRBP-R2A was created.

Standard sequence analysis indicated that the cDNA insert was 2615 base pairs long, with a 6 base pair 5' non-coding region followed by 1599 base pairs of coding region, and a 3'-non-coding region of 1010 base pairs. The sequence is set forth in SEQ ID NO: 1, including the deduced 533 amino acid sequence. The generated peptide sequences were both found in the deduced amino acid sequence.

EXAMPLE 14

Studies were carried out to determine if RBPr could be transcribed in vitro. To do so, the pRBP-R2A plasmid was linearized via HindIII, and mRNA obtained using RNA polymerase.

Figure 7:
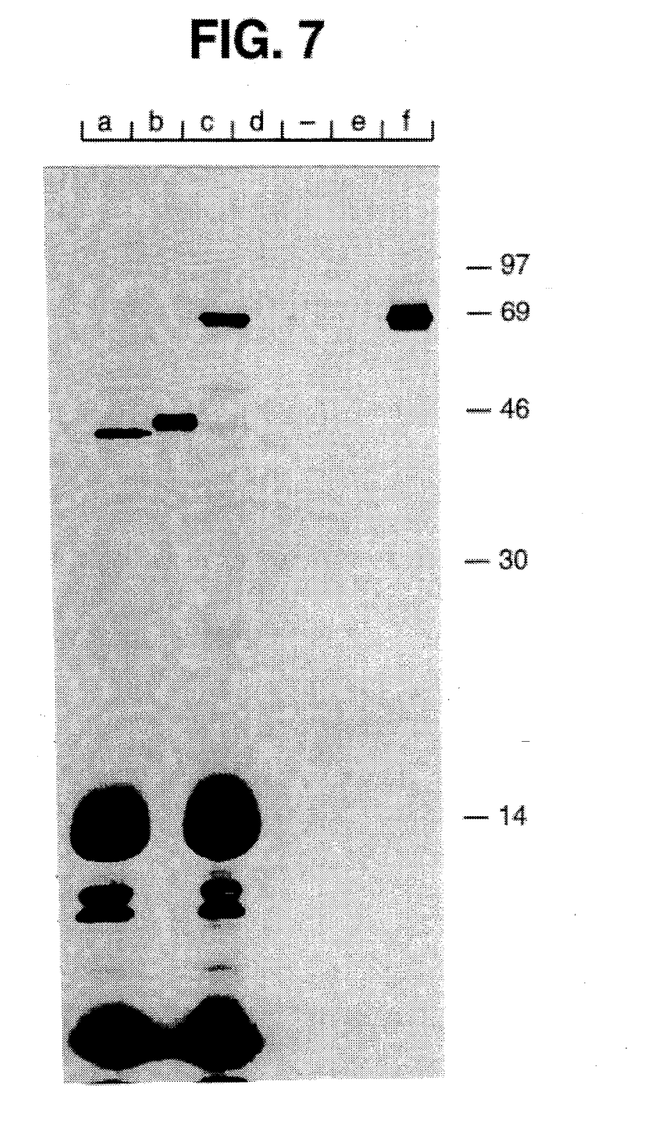
FIG. 7 displays results obtained following experiments designed to determine if RBPr could be transcribed in vitro. Supernatants from a rabbit reticulocyte lysate system were tested.

A rabbit reticulocyte lysate system with $^{35}S$-methionine, and either with or without dog pancreatic microsomes, was used (Levy et al., J. Cell Biol. 115:959–970 (1991)). Each translation reaction used 50–100 ng of mRNA, and a control was carried out, using HLA-B27 mRNA heavy chain, under identical conditions and in the presence of microsomal membranes. Membrane-associated proteins were then separated from unbound proteins via pelleting microsomes, using centrifugation at 14,000 xg for 10 minutes. Supernatants were collected and microsomes resuspended in PBS, washed, and centrifuged, followed by solubilization in 1% CHAPS. Aliquots of both supernatant and solubilized membrane associated protein were analyzed via SDS-PAGE. These results are shown in FIG. 7. Lanes c and d present the results secured for transcription of RBPr mRNA in the presence of dog pancreatic membranes, while lanes a and b show data for HLA-B27 mRNA under identical conditions. Lanes a and c are for unbound proteins, whereas lanes b and d are data for membrane bound material.

Only a small amount of RBPr associated with membrane, the larger portion remaining in lysate. The HLA-B27 protein did associate with the membranes, the signal sequence was cleaved and translated protein was glycosylated. These data suggest that RBPr is not efficiently integrated into heterologous membranes, further suggesting that additional factors may be necessary to secure the membrane bound form discussed supra—i.e., that observed in isolated RPE membrane fractions.

Lane f shows SDS-PAGE data for immunoprecipitation studies of in vitro synthesized RBPr, using mAb A52, and lane e shows an unrelated monoclonal. Immunoblot studies used solubilized proteins (1% CHAPS in PBS), using 5 ug of A52 mAb or 5ug of control Ig. This immunoprecipitation analysis confirms that pRBP.R2A encodes the RBPr recognized by mAb A52.

EXAMPLE 15

Figure 8:
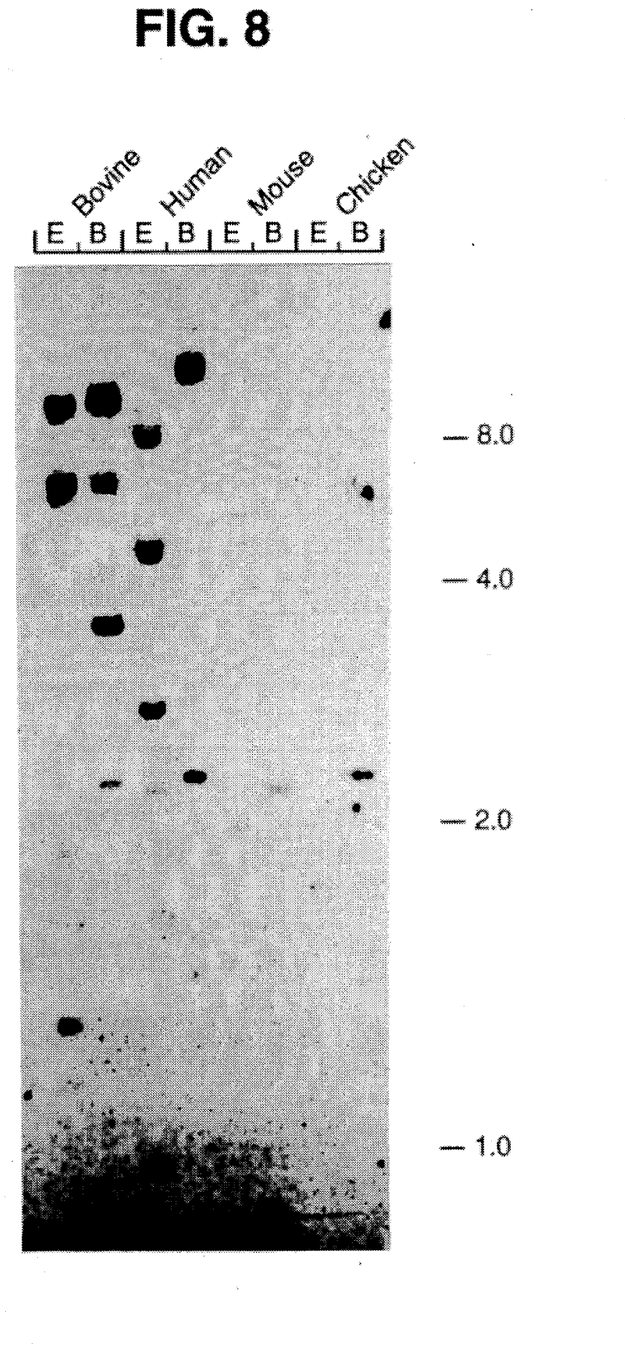
FIG. 8 shows the results of experiments to determine whether coding sequences for RBPr could be found in different species. High molecular weight DNA fractions were probed with the RBPr coding cDNA insert.

Studies were carried out in which high molecular weight DNA from bovine, human, mouse and chicken genomic DNAs was analyzed via Southern blot analysis. High molecular weight DNAs were completely digested with EcoRI, and subjected to electrophoresis using 1% agarose gel. The DNA was blotted onto Genescreen Plus filters (prehybridized in 6xSSC, 0.5% SDS, 5xDenhardt's and 100 ug/ml of salmon sperm, at 68° C.), and hybridized under stringent conditions with the entire RBPr coding cDNA insert from pRBP-R2A ($1\times10^6$ cpm labelled probe per ml solution). Following overnight hybridization, filters were washed in 2xSSC in 0.1% SDS at 68° C. for 15 minutes, and finally at 0.1xSSC in 0.1% SDS for an additional 15 minutes. Filters were exposed to Kodak XAR film using an intensifying Screen at −70° C. FIG. 8 presents the results of these experiments. Both bovine and human genomic DNAs show 5–6 easily identifiable bands of various intensity and length, while the number and intensity of binding were weaker in mouse and chicken genomes, but were nonetheless present. These data suggest that sequences for bovine and human genes are very similar, and also suggest the existence of a gene family.

EXAMPLE 16

The cDNA described supra was isolated, and additional experiments were carried out to isolate clones with longer 5' termini. To do so, 30,000 plaques of the RPE specific CDNA library was rescreened with a 30 mer oligonucleotide complementary to the 5' region of the sense strand of pRBP-R2A, i.e., nucleotide positions 27–57. The oligonucleotide was radiolabelled via T4 polynucleotide kinase.

Four extended clones were isolated and sequenced, and they are presented in SEQ ID NOS: 2–5. The extensions are:

SEQ ID NO: 2  GAGAAA
SEQ ID NO: 3  GCACCAACTG TGGACTGAGA GAAA
SEQ ID NO: 4  CAATCCTCTA CTGAGAGAAA
SEQ ID NO: 5  TCATCCTCTA CTGAGAGAAA.

EXAMPLE 17

Studies were carried out to determine distribution of receptors of the type described herein. This example, and example 18 which follows, should be considered together.

Figure 9:
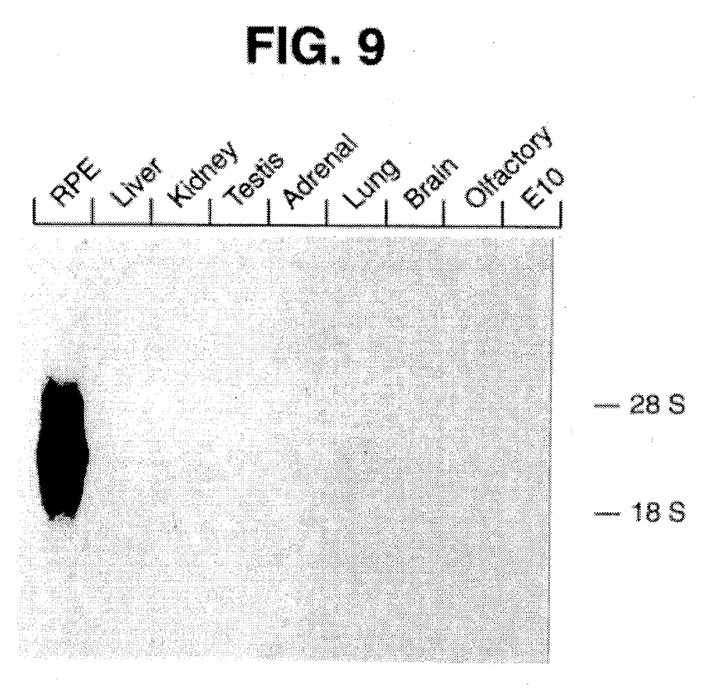
FIG. 9 sets forth the results of experiments where various tissues were tested with DNA probes for RBPr, to determine whether or not transcript was present.

Total RNA (20 ug) isolated from a series of tissues (bovine RPE, liver, kidney, testis, adrenal gland, lung, brain, olfactory epithelium and mouse embryo) was subjected to electrophoresis in a 1% gel containing formaldehyde. The separated RNA was blotted onto Hybond N filters and hybridized under stringent conditions, using the total insert of pRBP-R2A as probe. These results are shown in FIG. 9. RPE showed abundant hybridizing transcript, whereas all other tissues showed low, or undetectable levels. While several sizes of transcript were visualized, the most abundant transcripts are 3.2–3.6 kb in size, less abundant shorter and larger transcripts also being present, however.

EXAMPLE 18

Previous work has shown that RBP-receptor binding sites are present in membrane preparations from tissues other than RPE. In connection with this, and in view of the data of FIG. 9, polymerase chain reaction was carried out on testis and brain tissue. These experiments successfully amplified transcripts related to the RBPr cDNA described supra, supporting the hypothesis that RBPr is a member of a larger family of related molecules, i.e., receptors which bind to retinol binding protein, as well as other lipocalins. These data support the discussion presented in the "Background and Prior Art" section, supra, regarding the existence of a receptor system for the function of the lipocalins, retinol binding protein in particular. Thus, the invention relates to an isolated family of molecules, referred to collectively as receptors for retinol binding protein, as well as receptors for lipocalins. These receptors as the term is used herein, refer to proteinaceous molecules which are found in conjunction with cell membranes and facilitate the functioning of retinol binding protein. The term is used in its standard, art recognized sense, i.e., a molecule with high specific affinity for biologically active molecules, generally but not necessarily membrane bound. This definition does not include antibodies.

In addition to the isolated receptors, the invention also involves antibodies, both monoclonal and polyclonal, which specifically bind to these molecules, as well as nucleic acid sequences which code for the receptors.

The examples set forth supra deal, for the most part with the molecule referred to as RBPr, i.e., the retinol binding protein receptor found on the retina cells. Examples such as examples 17 and 18, however, point to the existence of other molecules which are equivalent to RBPr, leading to the conclusion that a family of molecules has now been identified. These molecules appear to be ubiquitous over mammalian species, e.g., as the examples show.

The different facets of the invention described herein are useful in various contexts. For example, both the antibodies and nucleic acid sequences can be used for phenotypic/genetic analysis to determine, e.g., if an individual suffers from a condition characterized by, e.g., inability to accumulate retinoids in the eye. This inability leads to retinitis pigmentosa. The various known functions of retinoids also suggests that various other retinoid linked pathological conditions may be diagnosed via assays for levels of the receptor associated with a particular retinol binding protein. Art recognized techniques may be used, such as immunoassays, DNA hybridization, PCR, and so forth, to determine whether receptor levels are too low or too high—i.e., are at variance with a normal level.

Identification of the nucleic acid sequences which code for receptors also permits one to assay for DNA mutation, such as point mutations, in the DNA of individuals suspected of being at risk or having diseases linked to aberrant receptors or receptor levels. Analysis may be undertaken via, e.g., PCR, Southern Blotting, RFLP analysis, etc. It also permits isolation of sequences which are homologous to sequences such as the one which codes for RBPr. These sequences can be found by carrying out hybridization experiments under stringent conditions (i.e., hybridization in 6xSSC, 0.5% SDS, 5xDenhardt's solution at 68° C., with 100 ug/ml of salmon sperm DNA, and a final wash with 0.3xSSC at 60° C.).

The receptors and antibodies may also be used in a therapeutic context, as it is well known that soluble receptors and antibodies may be used to prevent binding of a protein to its membrane-linked receptor. Thus, a subject characterized by enhanced levels of production of retinol binding protein may be treated via administering an amount of soluble receptor or antibody sufficient to inhibit binding of the retinol binding protein or other related molecule to its target. Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated nucleic acid molecule, the complementary sequence of which hybridizes to the nucleotide sequence set forth in SEQ ID NO: 1. under stringent conditions, wherein said isolated nucleic acid molecule codes for a mammalian retinol binding protein receptor which has a molecular weight of about 63 kilodaltons as determined by SDS-PAGE, wherein the mammalian retinol binding protein receptor binds to retinol binding protein, and said mammalian, retinol binding protein receptor is isolatable from mammalian retina.

2. The isolated nucleic acid molecule of claim 1, wherein said retinol binding protein receptor is a human retinol binding protein receptor.

3. The isolated nucleic acid molecule of claim 1, wherein said retinol binding protein receptor is a bovine retinol binding protein receptor.

4. The isolated nucleic acid molecule of claim 1, consisting of cDNA.

5. Expression vector comprising the nucleic acid molecule of claim 1, operably linked to a promoter.

6. Cell line transfected with the nucleic acid molecule of claim 1.

7. Isolated nucleic acid molecule consisting of the nucleotide sequence set forth in SEQ ID NO: 1.

8. Isolated nucleic acid molecule consisting of:

i) the nucleotide sequence set forth in SEQ ID NO: 1; and (ii) a nucleic acid molecule selected from the group consisting of (a) the molecule described the nucleotide sequence of SEQ ID NO: 2, (b) the molecule described by the nucleotide sequence of SEQ ID NO: 3, (c) the molecule described by the nucleotide sequence of SEQ ID NO: 4, and (d) the molecule described by the nucleotide sequence of SEQ ID NO: 5, wherein the nucleic acid molecule of (ii) is positioned 5' to the nucleic acid molecule of (i), and said nucleic acid molecules are linked to each other.

9. Expression vector comprising the nucleic acid molecule of claim 7, operably linked to a promoter.

10. Cell line transfected with the nucleic acid molecule of claim 7.

* * * * *

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 2629 bases
        ( B ) TYPE: nucleic acid
        ( C ) STRANDEDNESS: single
        ( D ) TOPOLOGY: linear     ( i i ) MOLECULE TYPE: cDNA to mRNA     ( i i i ) HYPOTHETICAL: no     ( i v ) ANTI-SENSE: no     ( x i ) SEQUENCE DESCRIPTION: SEQ ID NO: 1:

```
GAATTCGAG AAA                                                                                    13

ATG TCC AGC CAA GTT GAA CAT CCA GCT GGT GGT TAC AAG AAA CTG TTT                                  61
Met Ser Ser Gln Val Glu His Pro Ala Gly Gly Tyr Lys Lys Leu Phe
              5                   10                  15

GAA ACT GTG GAG GAA CTA TCC TCA CCG CTC ACA GCC CAT GTT ACA GGC                                 109
Glu Thr Val Glu Glu Leu Ser Ser Pro Leu Thr Ala His Val Thr Gly
             20                  25                  30

AGG ATC CCC CTC TGG CTA ACC GGC AGT CTC CTT CGA TGT GGG CCA GGA                                 157
Arg Ile Pro Leu Trp Leu Thr Gly Ser Leu Leu Arg Cys Gly Pro Gly
         35                  40                  45

CTC TTT GAG GTT GGA TCG GAA CCA TTT TAC CAC CTG TTT GAT GGG CAA                                 205
Leu Phe Glu Val Gly Ser Glu Pro Phe Tyr His Leu Phe Asp Gly Gln
     50                  55                  60

GCC CTC CTA CAC AAG TTT GAC TTT AAA GAA GGA CAT GTC ACA TAC CAC                                 253
Ala Leu Leu His Lys Phe Asp Phe Lys Glu Gly His Val Thr Tyr His
65                  70                  75                  80

AGA AGG TTC ATC CGC ACT GAT GCT TAC GTA CGG GCA ATG ACT GAG AAA                                 301
Arg Arg Phe Ile Arg Thr Asp Ala Tyr Val Arg Ala Met Thr Glu Lys
                         85                  90                  95

AGG ATC GTC ATA ACA GAA TTT GGC ACC TGT GCT TTC CCA GAT CCC TGC                                 349
Arg Ile Val Ile Thr Glu Phe Gly Thr Cys Ala Phe Pro Asp Pro Cys
                    100                 105                 110

AAG AAT ATA TTT TCC AGG TTT TTT TCT TAC TTC CGA GGA GTG GAG GTT                                 397
Lys Asn Ile Phe Ser Arg Phe Phe Ser Tyr Phe Arg Gly Val Glu Val
                115                 120                 125

ACT GAC AAT GCC CTT GTT AAT ATC TAC CCA GTG GGG GAA GAT TAC TAT                                 445
Thr Asp Asn Ala Leu Val Asn Ile Tyr Pro Val Gly Glu Asp Tyr Tyr
            130                 135                 140

GCC TGC ACA GAG ACC AAC TTC ATT ACA AAG GTT AAT CCT GAG ACC TTG                                 493
Ala Cys Thr Glu Thr Asn Phe Ile Thr Lys Val Asn Pro Glu Thr Leu
145                 150                 155                 160

GAA ACA ATT AAG CAG GTT GAC CTT TGC AAC TAT GTC TCA GTC AAT GGA                                 541
Glu Thr Ile Lys Gln Val Asp Leu Cys Asn Tyr Val Ser Val Asn Gly
                    165                 170                 175

GCC ACT GCT CAC CCC CAC ATT GAA AAT GAT GGG ACT GTT TAC AAC ATT                                 589
```

|     |     |     |     |     |     |     |     |     |     |     |     |     |     |     |     |
|-----|-----|-----|-----|-----|-----|-----|-----|-----|-----|-----|-----|-----|-----|-----|-----|
| Ala | Thr | Ala | His | Pro | His | Ile | Glu | Asn | Asp | Gly | Thr | Val | Tyr | Asn | Ile |
|     |     |     | 180 |     |     |     | 185 |     |     |     |     |     | 190 |     |     |

| GGT | AAT | TGC | TTT | GGG | AAA | AAT | TTT | TCA | ATT | GCC | TAC | AAT | ATT | GTA | AAG | 637 |
|-----|-----|-----|-----|-----|-----|-----|-----|-----|-----|-----|-----|-----|-----|-----|-----|-----|
| Gly | Asn | Cys | Phe | Gly | Lys | Asn | Phe | Ser | Ile | Ala | Tyr | Asn | Ile | Val | Lys |     |
|     |     | 195 |     |     |     |     | 200 |     |     |     |     | 205 |     |     |     |     |

| ATC | CCA | CCA | CTA | CAA | GCA | GAC | AAG | GAA | GAT | CCA | ATA | AGC | AAG | TCA | GAG | 685 |
| Ile | Pro | Pro | Leu | Gln | Ala | Asp | Lys | Glu | Asp | Pro | Ile | Ser | Lys | Ser | Glu |     |
|     | 210 |     |     |     |     | 215 |     |     |     |     | 220 |     |     |     |     |     |

| ATC | GTT | GTA | CAA | TTC | CCC | TGC | AGT | GAC | CGA | TTC | AAG | CCA | TCT | TAC | GTC | 733 |
| Ile | Val | Val | Gln | Phe | Pro | Cys | Ser | Asp | Arg | Phe | Lys | Pro | Ser | Tyr | Val |     |
| 225 |     |     |     |     | 230 |     |     |     |     | 235 |     |     |     |     | 240 |     |

| CAT | AGT | TTT | GGT | TTG | ACT | CCC | AAC | TAT | ATT | GTT | TTT | GTG | GAG | ACA | CCA | 781 |
| His | Ser | Phe | Gly | Leu | Thr | Pro | Asn | Tyr | Ile | Val | Phe | Val | Glu | Thr | Pro |     |
|     |     |     |     | 245 |     |     |     |     | 250 |     |     |     |     | 255 |     |     |

| GTC | AAA | ATT | AAT | CTG | TTC | AAG | TTT | CTT | TCT | TCA | TGG | AGT | CTT | TGG | GGA | 829 |
| Val | Lys | Ile | Asn | Leu | Phe | Lys | Phe | Leu | Ser | Ser | Trp | Ser | Leu | Trp | Gly |     |
|     |     |     | 260 |     |     |     |     | 265 |     |     |     |     | 270 |     |     |     |

| GCC | AAT | TAC | ATG | GAT | TGT | TTT | GAA | TCC | AAT | GAA | ACC | ATG | GGG | GTT | TGG | 877 |
| Ala | Asn | Tyr | Met | Asp | Cys | Phe | Glu | Ser | Asn | Glu | Thr | Met | Gly | Val | Trp |     |
|     |     | 275 |     |     |     |     | 280 |     |     |     |     | 285 |     |     |     |     |

| CTT | CAT | ATT | GCT | GAC | AAA | AAA | AGA | AAA | AAG | TAT | ATC | AAT | AAT | AAA | TAC | 925 |
| Leu | His | Ile | Ala | Asp | Lys | Lys | Arg | Lys | Lys | Tyr | Ile | Asn | Asn | Lys | Tyr |     |
|     | 290 |     |     |     |     | 295 |     |     |     |     | 300 |     |     |     |     |     |

| AGG | ACC | TCT | CCT | TTT | AAC | CTC | TTT | CAT | CAC | ATC | AAT | ACC | TAT | GAA | GAC | 973 |
| Arg | Thr | Ser | Pro | Phe | Asn | Leu | Phe | His | His | Ile | Asn | Thr | Tyr | Glu | Asp |     |
| 305 |     |     |     |     | 310 |     |     |     |     | 315 |     |     |     |     | 320 |     |

| CAT | GAG | TTT | CTG | ATT | GTG | GAT | CTC | TGT | TGC | TGG | AAA | GGA | TTT | GAA | TTT | 1021 |
| His | Glu | Phe | Leu | Ile | Val | Asp | Leu | Cys | Cys | Trp | Lys | Gly | Phe | Glu | Phe |     |
|     |     |     |     | 325 |     |     |     |     | 330 |     |     |     |     | 335 |     |     |

| GTT | TAT | AAT | TAT | TTA | TAT | TTA | GCC | AAT | TTA | CGT | GAG | AAC | TGG | GAA | GAG | 1069 |
| Val | Tyr | Asn | Tyr | Leu | Tyr | Leu | Ala | Asn | Leu | Arg | Glu | Asn | Trp | Glu | Glu |     |
|     |     |     | 340 |     |     |     |     | 345 |     |     |     |     | 350 |     |     |     |

| GTG | AAA | AAA | AAT | GCC | AGA | AAG | GCT | CCT | CAG | CCT | GAA | GTT | AGG | AGA | TAC | 1117 |
| Val | Lys | Lys | Asn | Ala | Arg | Lys | Ala | Pro | Gln | Pro | Glu | Val | Arg | Arg | Tyr |     |
|     |     | 355 |     |     |     |     | 360 |     |     |     |     | 365 |     |     |     |     |

| GTA | CTT | CCT | TTG | AAT | ATT | GAC | AAG | GCT | GAC | ACA | GGC | AAG | AAT | TTA | GTC | 1165 |
| Val | Leu | Pro | Leu | Asn | Ile | Asp | Lys | Ala | Asp | Thr | Gly | Lys | Asn | Leu | Val |     |
|     | 370 |     |     |     |     | 375 |     |     |     |     | 380 |     |     |     |     |     |

| ACA | CTC | CCC | AAC | ACA | ACT | GCC | ACT | GCA | ATT | CTG | TGC | AGT | GAC | GAG | ACC | 1213 |
| Thr | Leu | Pro | Asn | Thr | Thr | Ala | Thr | Ala | Ile | Leu | Cys | Ser | Asp | Glu | Thr |     |
| 385 |     |     |     |     | 390 |     |     |     |     | 395 |     |     |     |     | 400 |     |

| ATC | TGG | CTG | GAA | CCT | GAG | GTT | CTC | TTT | TCA | GGG | CCT | CGC | CAA | GCA | TTT | 1261 |
| Ile | Trp | Leu | Glu | Pro | Glu | Val | Leu | Phe | Ser | Gly | Pro | Arg | Gln | Ala | Phe |     |
|     |     |     |     | 405 |     |     |     |     | 410 |     |     |     |     | 415 |     |     |

| GAG | TTT | CCT | CAA | ATC | AAT | TAC | CAG | AAG | TAT | GGT | GGG | AAA | CCT | TAC | ACA | 1309 |
| Glu | Phe | Pro | Gln | Ile | Asn | Tyr | Gln | Lys | Tyr | Gly | Gly | Lys | Pro | Tyr | Thr |     |
|     |     |     | 420 |     |     |     |     | 425 |     |     |     |     | 430 |     |     |     |

| TAT | GCA | TAT | GGA | CTT | GGC | TTG | AAT | CAC | TTT | GTT | CCA | GAC | AGG | CTC | TGT | 1357 |
| Tyr | Ala | Tyr | Gly | Leu | Gly | Leu | Asn | His | Phe | Val | Pro | Asp | Arg | Leu | Cys |     |
|     |     | 435 |     |     |     |     | 440 |     |     |     |     | 445 |     |     |     |     |

| AAG | CTG | AAC | GTC | AAA | ACT | AAA | GAA | ACC | TGG | GTA | TGG | CAA | GAG | CCT | GAT | 1405 |
| Lys | Leu | Asn | Val | Lys | Thr | Lys | Glu | Thr | Trp | Val | Trp | Gln | Glu | Pro | Asp |     |
|     | 450 |     |     |     |     | 455 |     |     |     |     | 460 |     |     |     |     |     |

| TCA | TAC | CCC | TCA | GAA | CCT | ATC | TTT | GTT | TCT | CAC | CCA | GAT | GCC | TTG | GAG | 1453 |
| Ser | Tyr | Pro | Ser | Glu | Pro | Ile | Phe | Val | Ser | His | Pro | Asp | Ala | Leu | Glu |     |
| 465 |     |     |     |     | 470 |     |     |     |     | 475 |     |     |     |     | 480 |     |

| GAA | GAT | GAC | GGT | GTA | GTT | CTG | AGT | GTG | GTG | GTG | AGC | CCT | GGG | GCA | GGA | 1501 |
| Glu | Asp | Asp | Gly | Val | Val | Leu | Ser | Val | Val | Val | Ser | Pro | Gly | Ala | Gly |     |
|     |     |     |     | 485 |     |     |     |     | 490 |     |     |     |     | 495 |     |     |

| CAA | AAG | CCT | GCT | TAT | CTT | CTG | ATT | CTG | AAT | GCC | AAG | GAC | TTG | AGT | GAA | 1549 |

| Gln | Lys | Pro | Ala | Tyr | Leu | Leu | Ile | Leu | Asn | Ala | Lys | Asp | Leu | Ser | Glu | |
|-----|-----|-----|-----|-----|-----|-----|-----|-----|-----|-----|-----|-----|-----|-----|-----|-----|
|     |     | 500 |     |     |     |     |     | 505 |     |     |     |     | 510 |     |     |     |

| GTT | GCC | AGG | GCT | GAA | GTG | GAG | ATT | AAC | ATC | CCC | GTC | ACC | TTT | CAT | GGA | 1597 |
|-----|-----|-----|-----|-----|-----|-----|-----|-----|-----|-----|-----|-----|-----|-----|-----|------|
| Val | Ala | Arg | Ala | Glu | Val | Glu | Ile | Asn | Ile | Pro | Val | Thr | Phe | His | Gly |      |
|     |     | 515 |     |     |     |     | 520 |     |     |     |     | 525 |     |     |     |      |

| CTG | TTC | AAA | AAA | TCC | 1612 |
|-----|-----|-----|-----|-----|------|
| Leu | Phe | Lys | Lys | Ser |      |
|     | 530 |     |     |     |      |

```
TGAGCACATT CTAGCATGAC ATGTTTCTGG TGACAAAACA CAGAGAAACG TAGTTAGGTC    1672
TGCAATCAAA TTCTGTTTAG CTTTAGCCTG CTGTCTATAA GGGTTTTAAC TTGCAGATGC    1732
ACACCGTTTT GCAGTATTTT ACAGAAAGCA CAGAGTTGAG TAAGGAATTC CTTTTAAAAA    1792
AGTGCTTATT TAGATAATCG TACTTCGTGA GACAGGCACA TCATAACTAA AAACTCTTTA    1852
TATATTTACA ATCAAATAGA AAATGAATGT GAATTTATTA AACTGTTTTT CATTCCTATT    1912
ATAAAAGTGT ATTTTAGGCA CCCATCTACT CCTATTACTT TTTAACATTT AAAAGCCAAA    1972
GTCCTCTACA GCTGATATGT ATATAGCTTT GCTGTGTCAA GGCAGCATCT TGGAAAAAGG    2032
CTTAGTTACT AAATGTCAAA TCAAACTTCT TCTCAAACCA GGGACTTTGA TCTAAGACAA    2092
TCATTGTAAT TGTATGCACA TATGTATTAT TATTCAAAGA TTCTCATGGT TTAAACTTTA    2152
ATATTTCCAT TTAATATAGG CAATTATTAC TATTTCTGAT TTCACAGTAA GGAAGCCTGT    2212
TTCTAAGTCA CTGAGGGCTG TCAACCAAAT ACCTTCTCAG AGATTACATT ATCTATTAGA    2272
AACTTATATA ACATAAAAGC AATTACATAT AGTAGTGACT ATTTTTTTA AATAGCATAA     2332
AATACTTACA AACATAATTG CTGTTTAAAA TCAGATTATG GGGATAATAA TGTGTATGGG    2392
GGGGGTTATA CTTTGTTGCC TCTTCTGCTT AATTACATTT AAGCACTGTG CACCTGACTG    2452
AAGAGAAAAT GAGAAAATAG AAAATACTGT CATTAATGTT CAGATATGAA TATAGTTTAA    2512
GCACTTTTGT TTTTAAAATT ATTCTTTTCT GAGATACATG TTGCAAAAAA AATGAAGATT    2572
GACAAAAATT TTTATTCTAT ATCTTAATCC TGTTTGACTA AGTAAAAACA GCTTGAA       2629
```

( 2 ) INFORMATION FOR SEQ ID NO: 2:

( i ) SEQUENCE CHARACTERISTICS:
        ( A ) LENGTH: 6 bases
        ( B ) TYPE: nucleic acid
        ( C ) STRANDEDNESS: single
        ( D ) TOPOLOGY: linear     ( i i ) MOLECULE TYPE: cDNA to mRNA     ( i i i ) HYPOTHETICAL: no     ( i v ) ANTI-SENSE: no     ( x i ) SEQUENCE DESCRIPTION: SEQ ID NO: 2:

GAGAAA                                                          6

( 2 ) INFORMATION FOR SEQ ID NO: 3:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear     ( i i ) MOLECULE TYPE: cDNA to mRNA     ( i i i ) HYPOTHETICAL: no     ( i v ) ANTI-SENSE: no     ( x i ) SEQUENCE DESCRIPTION: SEQ ID NO: 3:

GCACCAACTG TGGACTGAGA GAAA 24

(2) INFORMATION FOR SEQ ID NO: 4:

(i) SEQUENCE CHARACTERISTICS:
        (A) LENGTH: 20 bases
        (B) TYPE: nucleic acid
        (C) STRANDEDNESS: single
        (D) TOPOLOGY: linear     (ii) MOLECULE TYPE: cDNA to mRNA     (iii) HYPOTHETICAL: no     (iv) ANTI-SENSE: no     (xi) SEQUENCE DESCRIPTION: SEQ ID NO: 4:

CAATCCTCTA CTGAGAGAAA 20

(2) INFORMATION FOR SEQ ID NO: 5:

(i) SEQUENCE CHARACTERISTICS:
        (A) LENGTH: 20 bases
        (B) TYPE: nucleic acid
        (C) STRANDEDNESS: single
        (D) TOPOLOGY: linear     (ii) MOLECULE TYPE: cDNA to mRNA     (iii) HYPOTHETICAL: no     (iv) ANTI-SENSE: no     (xi) SEQUENCE DESCRIPTION: SEQ ID NO: 5:

TCATCCTCTA CTGAGAGAAA 20